US009867732B2

(12) United States Patent
Mokrane

(10) Patent No.: US 9,867,732 B2
(45) Date of Patent: *Jan. 16, 2018

(54) BODY FLUID MANAGEMENT SYSTEM

(71) Applicant: Mohamed Mokrane, Alger (DZ)

(72) Inventor: Mohamed Mokrane, Alger (DZ)

( * ) Notice: Subject to any disclaimer, the term of this patent is extended or adjusted under 35 U.S.C. 154(b) by 0 days.

This patent is subject to a terminal disclaimer.

(21) Appl. No.: 14/823,347

(22) Filed: Aug. 11, 2015

(65) Prior Publication Data

US 2016/0199213 A1    Jul. 14, 2016

Related U.S. Application Data

(63) Continuation of application No. 13/639,858, filed as application No. PCT/DZ2011/000002 on Apr. 6, 2011, now Pat. No. 9,101,490.

(30) Foreign Application Priority Data

Apr. 8, 2010  (DZ) .......................... 100198

(51) Int. Cl.
| | |
|---|---|
| *A61F 5/453* | (2006.01) |
| *A61F 5/442* | (2006.01) |
| *A61F 5/451* | (2006.01) |
| *A41B 9/02* | (2006.01) |
| *A61H 33/00* | (2006.01) |
| *A61H 35/00* | (2006.01) |

(52) U.S. Cl.
CPC .............. *A61F 5/451* (2013.01); *A41B 9/023* (2013.01); *A61F 5/442* (2013.01); *A61H 33/00* (2013.01); *A61H 35/00* (2013.01)

(58) Field of Classification Search
CPC .................................. A61F 5/442; A61F 5/451
See application file for complete search history.

(56) References Cited

U.S. PATENT DOCUMENTS

| | | | | |
|---|---|---|---|---|
| 3,397,698 | A * | 8/1968 | Hickey ................... | A61F 5/453 604/353 |
| 4,270,231 | A * | 6/1981 | Zint ........................ | A61G 9/006 4/144.1 |
| 5,009,649 | A * | 4/1991 | Goulter ................... | A61F 5/453 604/349 |
| 5,334,174 | A * | 8/1994 | Street ...................... | A61F 5/451 2/2.11 |
| 5,797,890 | A * | 8/1998 | Goulter ................... | A61F 5/453 604/351 |
| 8,357,132 | B1 * | 1/2013 | Lekweuwa ........... | A61F 5/4408 604/349 |
| 8,608,717 | B2 * | 12/2013 | Tung ....................... | A61F 5/453 604/346 |
| 2007/0123833 | A1 * | 5/2007 | Bruns ...................... | A61F 5/451 604/349 |
| 2009/0270822 | A1 * | 10/2009 | Medeiros ................ | A61F 5/453 604/347 |
| 2011/0152802 | A1 * | 6/2011 | DiCamillo .............. | A61F 5/453 604/349 |
| 2014/0350501 | A1 * | 11/2014 | Garcia Calero ........ | A61F 5/453 604/353 |

* cited by examiner

*Primary Examiner* — Susan Su
(74) *Attorney, Agent, or Firm* — Mark M. Friedman

(57) ABSTRACT

A system for managing and controlling bodily fluids such as urine and menstrual flow includes a garment with a latex envelope, for receiving the fluids from the male or female genitalia, and a system for disinfecting the male or female genitalia within the envelope.

3 Claims, 6 Drawing Sheets

Figure 1:
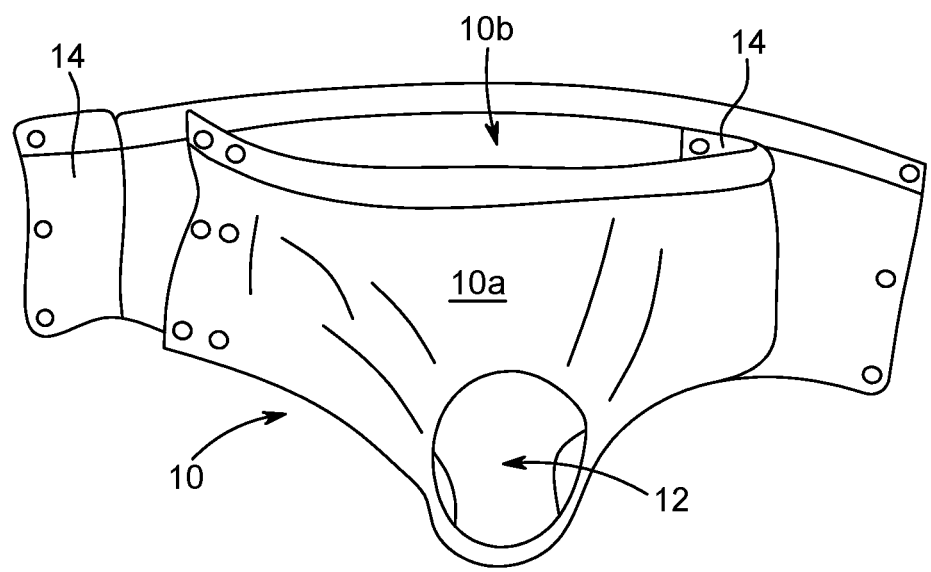
Figure 2:
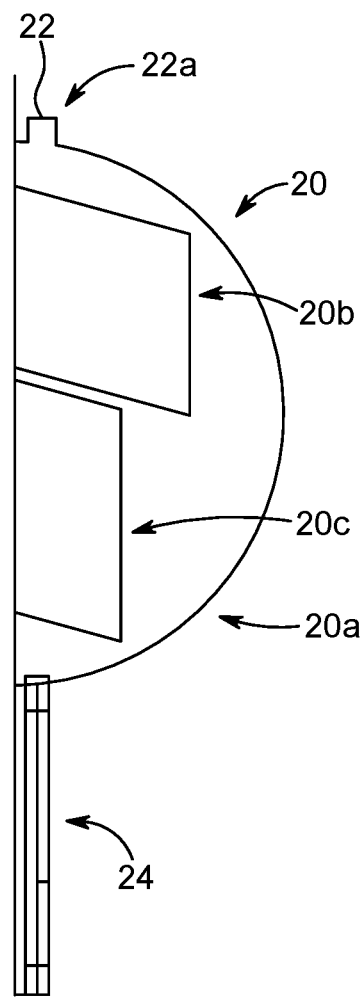
Figure 3:
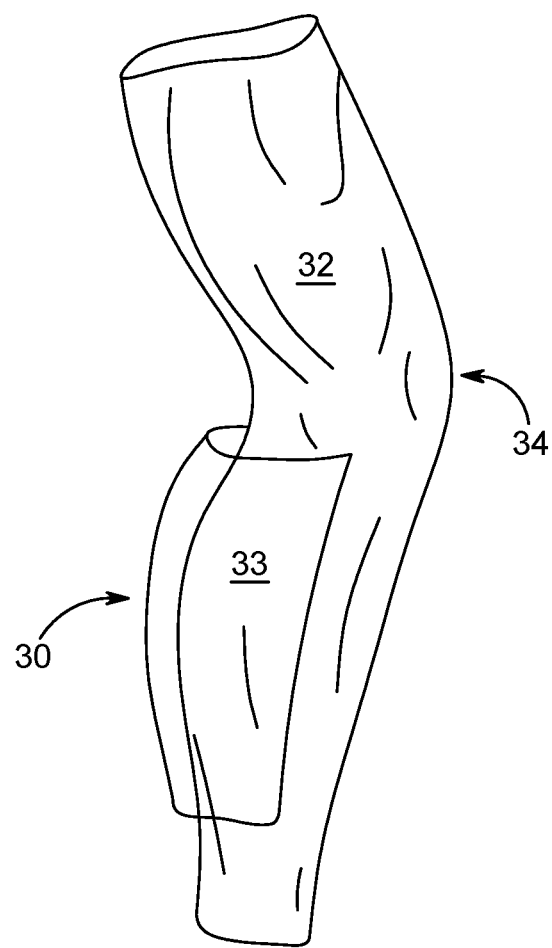

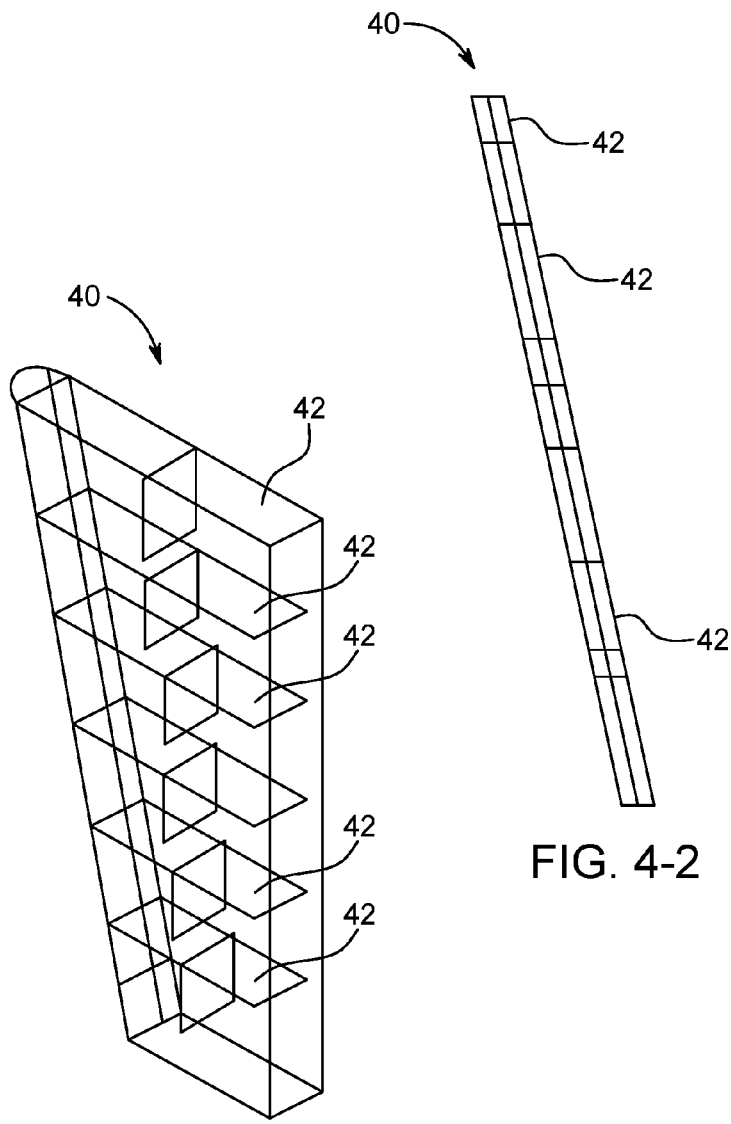
FIG. 4-1
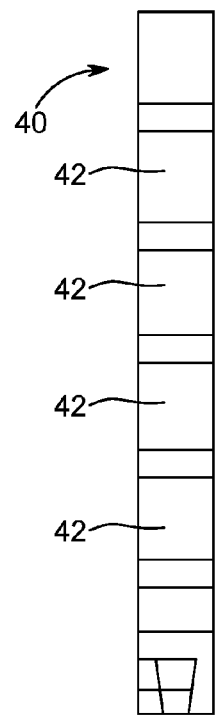
FIG. 4-2
FIG. 4-3
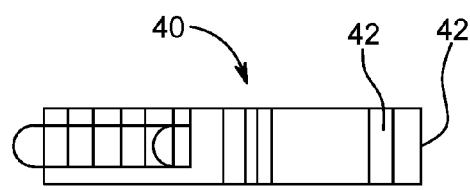
FIG. 4-4
FIG. 4

BODY FLUID MANAGEMENT SYSTEM

This application is a Continuation Patent Application of commonly owned U.S. patent application Ser. No. 13/639,858, entitled: Body Fluid Management System, filed on Oct. 6, 2012, now U.S. Pat. No. 9,101,490, the disclosure of which is incorporated by reference in its entirety herein.

TECHNICAL FIELD

Control of handicapping liquids consists of a device for the complete management of the flow of voluntary or involuntary urine, and the menstrual flow cycle for women in daily life, allowing for men and women to move unobtrusively.

BACKGROUND

For the management of incontinence of disposable absorbent plastic diapers, some of which for women, have a powder to freeze the urine and avoid overflow, there exists a system called PENI-FLOW™ connected to a collector, which is presently used.

SUMMARY OF THE INVENTION

The aim of the invention is to restore a normal quality of life for patients to manage incontinence, and for women to manage menstrual flow in order to allow them to move freely. As the invention allows Muslims a permanent hygiene, they achieve the accomplishment of ablution for their prayers. At the holy places of Islam at Mecca, during the days of Hajj, the invention allows its users to stabilize their movements, which will increase the area and therefore the number of pilgrims in Mina and Arafat Djebel, and avoid contacts reducing the contagious diseases epidemics to increase the safety of people and give them more rest.

The equipment of the present invention is autonomous, hermetic, lightweight, comfortable and discreet, and has a system of cleaning and sanitizing the penis and removal after urination, with an option of back pack tank with telescopic faucet, which can also perform the ritual of purification of body parts by water in this case of occurrence of ablutions for Muslims.

DESCRIPTION OF THE DRAWING FIGURES AND THE INVENTION

Figure 6:
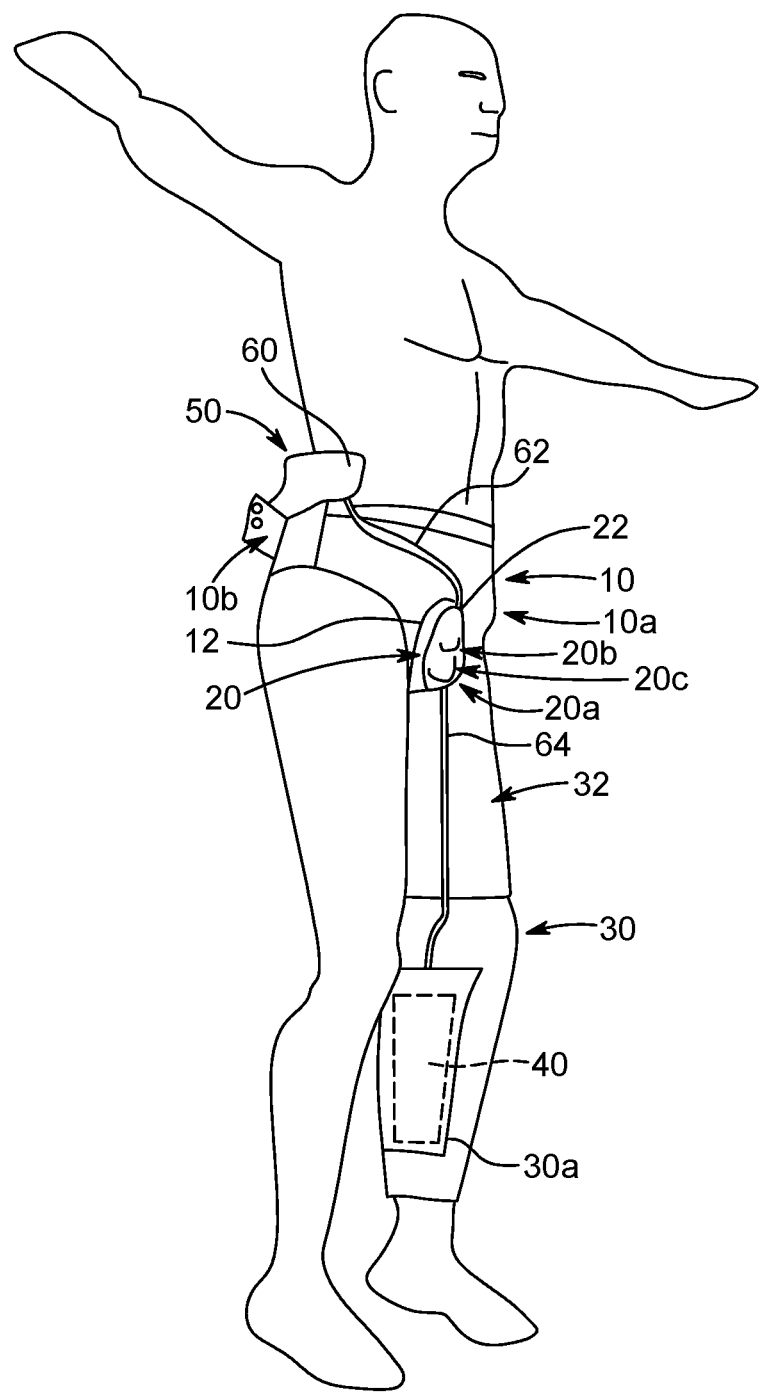

FIG. 1 shows a Main Slip The main slip 10 consists of a slip or shorts 10 with an opening 12 for fixing the fringe of the envelope 20 (FIG. 2) to the skin, the envelope 20 serving as a urinal. Side openings 14, to defecate without the system being de-taped, keeping the front part 10a of the slip 10 which becomes independent of the rear part 10b. There is also an adjustable belt for the support of a wash pump 60 (FIG. 6).

FIG. 2 shows a Latex Envelope 20. The envelope 20 is of to curved plane shaped like a half ellipsoid (having undergone a rotation about the major axis).

On this envelope 20 three parts 20a-20c are attached, which are:

a) The domed membrane 20a and flask that acts as a urinal in its outer part.

b) The sleeve 20b at the top (It is open) receiving the penis.

c) The bottom pocket 20c to accommodate the scrotum:

The position of pans 20b and 20c will be the one for the use of the envelope 20 after loosening the mould (actually in the mould, the two parties will be reversed).

An opening 22 in a stub 22a at the top of the envelope 20 is reserved for the tube (line) 62 (FIG. 6) penetrating into the envelope 20. In fact the tube 62 enters the stub 22a secured to the envelope. The stub 22a is cylindrical and is 5 mm in height and 5 mm in diameter.

The bottom tube (line) 64 coming out of the envelope 20 has an opening 24 having the shape of an inverted pyramid. This opening 24 acts as a funnel. This pyramid is formed of two sides of an equal and symmetrical trapezoid.

The elliptical flat surfaced part on the inner side of the envelope 20, matches the shape of the half ellipsoid. The extension of the surface part is a fringe, which extends an extra 3 cm for the attachment of the envelope 20 to the main slip 10 opening 12.

FIG. 3 shows a Knee Brace 30. The knee brace 30 is a holder (with a pocket 30a, as shown in FIG. 5) for a collector 40 (FIG. 4), and is attached to the leg 32, for example, the calf 33, proximate to the knee 34.

FIG. 4 shows a Collector 40 in four views as FIGS. 4-1, 4-2, 4-3 and 4-4. The Collector or collector packet 40 consists of honeycombs 42 in the form of hubbies or a hemisphere cut along a diameter, the bubbles which communicate with each other in order to avoid backflow during the receipt and storage of liquids. The collector packet 40 is hermetic, flexible and/or elastic.

Figure 5:
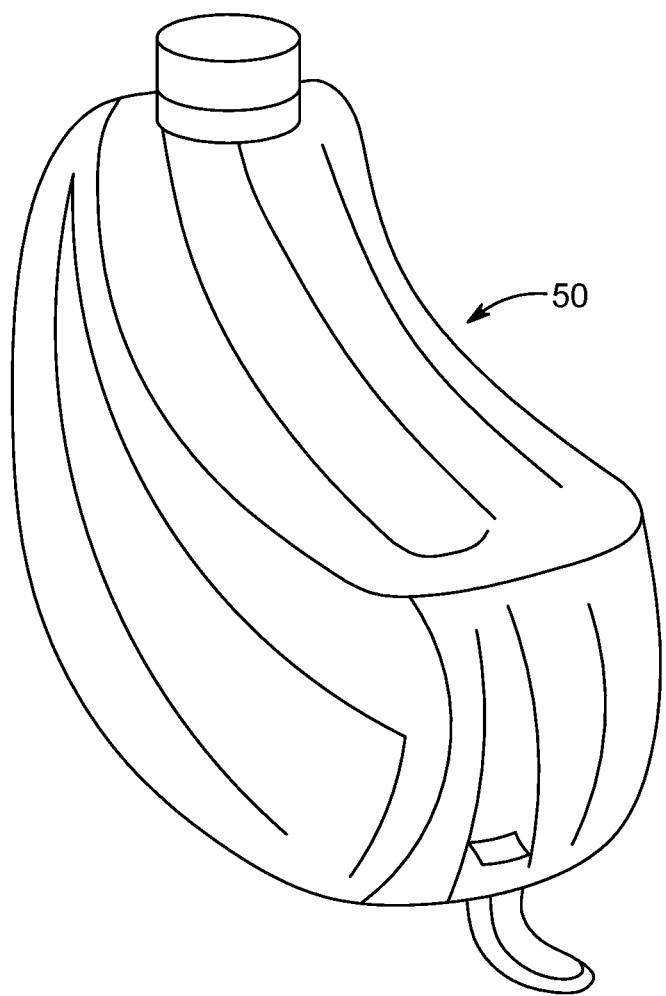

FIG. 5 shows a Tank 50. A rectangular pump 60 is in the tank 50, the pump 60 connects to a container which is for the carrying the washing and disinfection liquid for women to avoid microbial infection. The tank 50 is equipped with an exit hatch valve and a filling mouth and a tube 62 connecting the container of the tank 50 to the envelope 20 in its upper part. The pump 60 works by manual pressure and operates whenever needed.

FIG. 6 shows the present invention as worn by a male user.

ADDITIONAL COMPONENTS

A container is located in the tank 50, which is positioned above the envelope 20 and placed so as to send the liquid with a strong flow of washing and disinfecting liquid through the tube 62.

The bottom tube 64 connecting the envelope 20 to the collector 40 is flat to accommodate high fluid flow. The bottom tube 64 extends from the funnel 24, which is the lower end of the envelope 20. The tube 62 connecting the pump 60 to the envelope 20 is conventionally rounded.

c) Valves:

There are four valves, the first two have different sizes have identical functions.

The collector valve comprises of a flap, which opens inwards, and serves to clamp the non return valve of the flat outlet nozzle coming from the envelope 20.

A pump valve is used to release the liquid for washing or disinfection by manual pressure (on the pump 60 and made of soft rubber). Its role is to stop the liquid or release it during the application of manual pressure.

A Non-return valve, is located at the end of the bottom tube 64, which connects the envelope 20 to the collector 40.

An Air discharge valve functions to release the air whilst preventing liquids to pass, facilitating the movement of liquid and evacuation to the collector 40. This valve will be located on the upper level of the envelope 20 about 10 mm cylindrical stump 22a. This valve is similar to those used in aquariums.

The adhesive to be used is a double-sided hypoallergenic adhesive. This adhesive serves to seal and close the urinal envelope 20 hermetically. The adhesive has a width of 15 mm for the man; it will take an elliptical shape so as to pass around the sleeve 20b of the penis and the scrotum pocket 20c. For the woman the side of the envelope 20 extends approximately 15 mm in an oval around the genital area.

An Ablutions Jacket is made of a single piece of latex material of a rectangular shape, where a two pocket water tank may be attached with two straps and a belt, with a 40 cm telescopic pipe, at its end a 7 cm valve rod with as half-circle, for performing closing and opening functions.

The invention is a system, shown being worn, for example, in FIG. 6, that can manage comprehensively, incontinence, and menstrual flow of women, to provide the user the independence to urinate anywhere and at any time, even while moving.

The system has the following elements, including a slip 10, with as urinal envelope 20 with a slot for the penis 20b and scrotum 20c. A knee brace 30 with pockets 30a for the support of honeycomb collectors 40 to avoid backflow effects. A manual pump 60 associated with a fluid tank 50, for washing and disinfection of genitals, including post urination and menstruation. The collector 40 is partitioned into honeycombs 42, and has a large storage capacity and includes, pipes and valves.

There is also a back pack jacket (not shown) which has straps and a fastening belt (not shown). This jacket is designed to store water for the ablutions. It is equipped with a telescopic metal tube with half-moon designed faucet that can open and close in a flexible manner.

Methods for Manufacturing the Invention

Making the invention consists of moulding process of the following parts: the envelope 20 including the penis 20b and scrotum 20c holder, in latex, by steeping technology. Moulding of hand pump 60 in soft rubber is performed by injection molding or press technology. Moulding of the honeycomb collector 40 is performed by injection molding or press technology in plastic. The knee brace 30 is made with thin latex or elastic resistant fabrics. The bottom tube 64 is made of latex to accommodate high flows. The Ablutions jacket is crafted in thin latex with straps and belts along with a telescopic tube.

Application

This invention relates to both the sexes, adolescents and adults. As shown, for example, in FIG. 6, with reference also to FIGS. 1-5, use of the invention begins by placing the slip 10 as a panty and taping the edge of the envelope 20 around the penis and scrotum, with a double-sided anti-allergenic, medical adhesive, and then, adjusting the envelope 20 in the slip 10 according to the measurements by the side openings. The tank 50/pump 62 is placed on the left hip in the hip belt and connect the washing pipe. The knee brace 30 is attached above the knee 34 to the ankle. The honeycomb collector 40 is connected e to the flow tube 62, this flow tube 62 provided with a non return valve, which is places in a pocket 30a of the knee brace 30.

The user or patient dresses as or wears the slip 10.

The user adjusts the device according to his size by the belts of the side openings. He places his penis in the urinal envelope 20 sleeve 20b and places the scrotum into the pocket 20c. The envelope 20 is sealed to the skin by taping the envelope 20 to the skin with double-sided tape.

The male user then sets the knee brace 30, fixes the pump 62, and attaches the collector 40 to the tip of the tube 62. When the user urinates, the flow is handled hermetically. First, the penis empties the urine in the urinal envelope 20, where it passes through the tube 62 along the inner thigh to flow into the collector 40. For women, fluid flow, urine or menstrual, is managed identically.

Then, the user or patient manually activates the pump 62, and pressure, acting on the opening valve, releases the pressurized liquid distributed by the container of the tank 50, for effective cleaning and disinfection of the genitals by water that contains an antiseptic. The disinfectant also cleans the tubes 62, 64 the same way as the genitals. The collector 40 is of a large capacity by design, and once filled, is detached from the tube 62. The valve automatically closes and the collector 40 is hermetically sealed to be thrown in the trash without risk of damage. The collector 40 is quickly replaced by a spare collector 40 and reinserted into the pocket of the knee brace 30.

The side openings of the slip 10 allow patients in defecate without de-taping the envelope 20, and adjusting the measurements.

The invention claimed is:

1. A method for cleansing genitalia, comprising:
   obtaining a wearable system comprising:
      an undergarment including an open area configured for supporting a fluid receiver, the fluid receiver being adapted to cover genitalia of a male user, the fluid receiver comprising a membrane, the membrane including portions configured for separately accommodating the penis and scrotum, defining the genitalia; an inlet opening located on the membrane; and, an outlet opening located on the membrane;
      a wearable storage unit for holding washing fluid, the wearable storage unit configured to supply fluid to the fluid receiver via the inlet opening;
      a collector in fluid communication with the fluid receiver via the outlet opening, the collector configured to receive fluid from the fluid receiver; and,
      a pump in communication with the fluid receiver and the wearable storage unit, the pump, when activated, provides fluid from the wearable storage unit to the fluid receiver for cleaning the genitalia; and,
   activating the pump to bring the washing fluid into the membrane through the inlet opening such that the water flows in the membrane to wash the separated penis and scrotum, and continues to flow out of the membrane through the outlet opening into the collector.

2. The method of claim 1, additionally comprising: removing the collector when an amount of fluid has accumulated therein.

3. The method of claim 2, additionally comprising: replacing the collector by a spare collector to the wearable system where the collector was removed.

* * * * *